United States Patent [19]

Boisde et al.

[11] Patent Number: 4,907,037
[45] Date of Patent: Mar. 6, 1990

[54] ACTIVE CHEMICAL TRANSDUCER WITH OPTICAL FIBRES AND REAGENT SUPPORTING MEANS

[75] Inventors: Gilbert Boisde, Bures Sur Yvette; Jean-Jacques Perez, Chattillon, both of France

[73] Assignee: Commissariat A L'Energie Atomiqued, Paris, France

[21] Appl. No.: 169,958

[22] Filed: Mar. 18, 1988

[30] Foreign Application Priority Data

Mar. 27, 1987 [FR] France ................................. 87 04299

[51] Int. Cl.⁴ ..................... G01N 21/78; G01N 21/80; G01N 33/52
[52] U.S. Cl. .............................. 356/412; 250/227.28; 422/56; 422/58
[58] Field of Search .................. 356/44, 412; 250/227; 422/56, 58

[56] References Cited

U.S. PATENT DOCUMENTS

| | | | |
|---|---|---|---|
| 4,223,226 | 9/1980 | Quick et al. | 356/44 X |
| 4,295,470 | 10/1981 | Shaw et al. | 128/634 |
| 4,517,456 | 5/1985 | Halsall et al. | 250/227 X |
| 4,557,900 | 12/1985 | Heitzmann | 422/56 X |
| 4,560,248 | 12/1985 | Cramp et al. | 422/58 X |
| 4,577,109 | 3/1986 | Hirschfeld | 250/461.1 |
| 4,682,895 | 7/1987 | Costello | 422/58 X |
| 4,760,250 | 7/1988 | Loeppert | 250/227 |

FOREIGN PATENT DOCUMENTS 0072627 7/1982 European Pat. Off. .

OTHER PUBLICATIONS

Article by W. R. Seitz published in Analytical Chemistry, vol. 56, No. 1, Jan. 1984, pp. 16A–34A.
Article by T. Hirschfeld published in "Advance in Instrumentation", vol. 40, 1st part, 1985, pp. 305–317.

*Primary Examiner*—Vincent P. McGraw
*Attorney, Agent, or Firm*—James E. Nilles

[57] ABSTRACT

It is intended for measuring a given characteristic of a fluid medium and comprises at least one assembly having an appropriate reagent for said measurement and serving to interact with the fluid medium, reagent support means, an optical fibre (2) called the emitting fibre and used for transmitting light in the direction of the support means and at least one other optical fibre (4), called the receiving fibre and which recovers at least part of the light from the support means when the latter receive the light from the emitting fibre. The support means comprise a single porous or adsorbant element (10) to which is fixed the reagent and which is positioned facing the emitting fibre and each receiving fibre. This element is in direct contact with the fluid medium when the transducer is immersed in it and therefore has no confinement membrane.

21 Claims, 2 Drawing Sheets

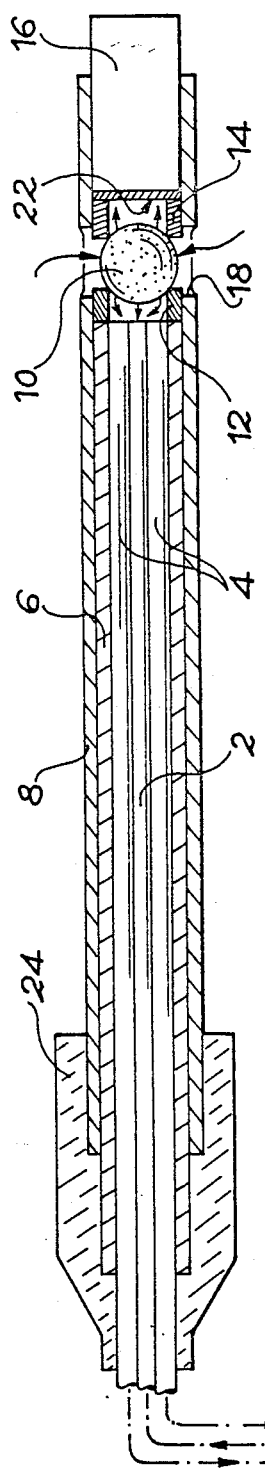
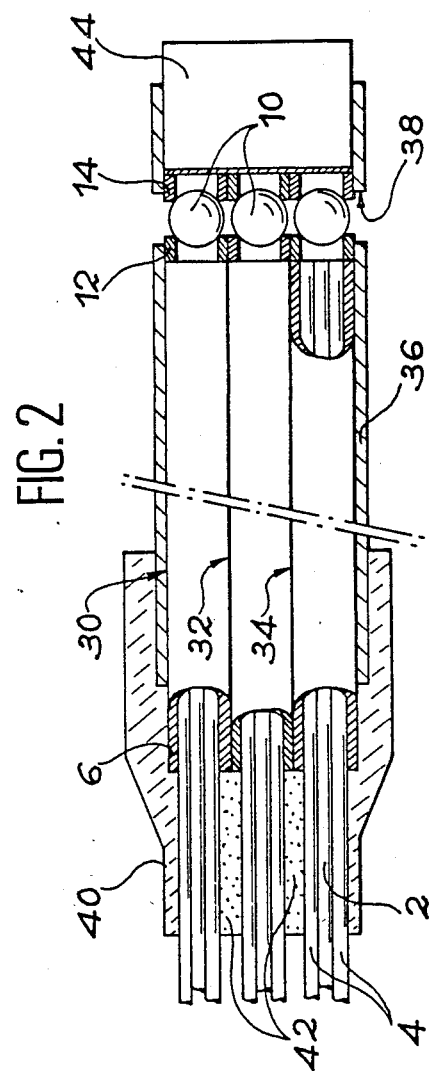

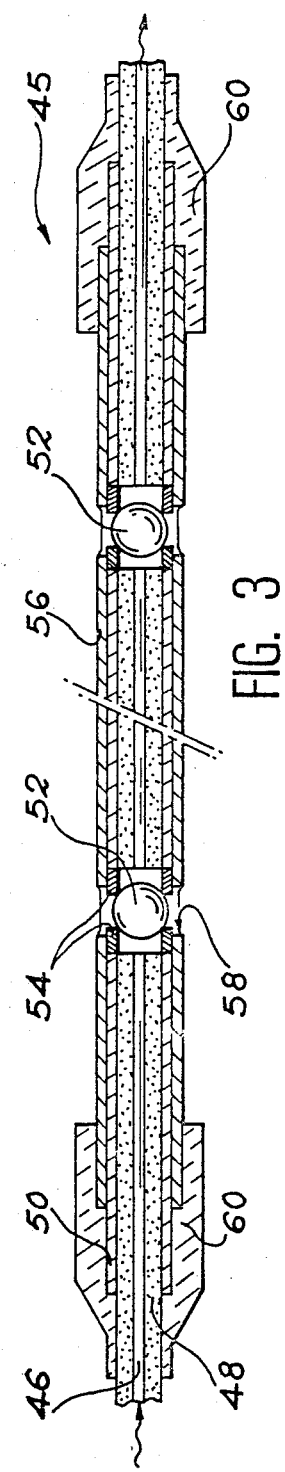
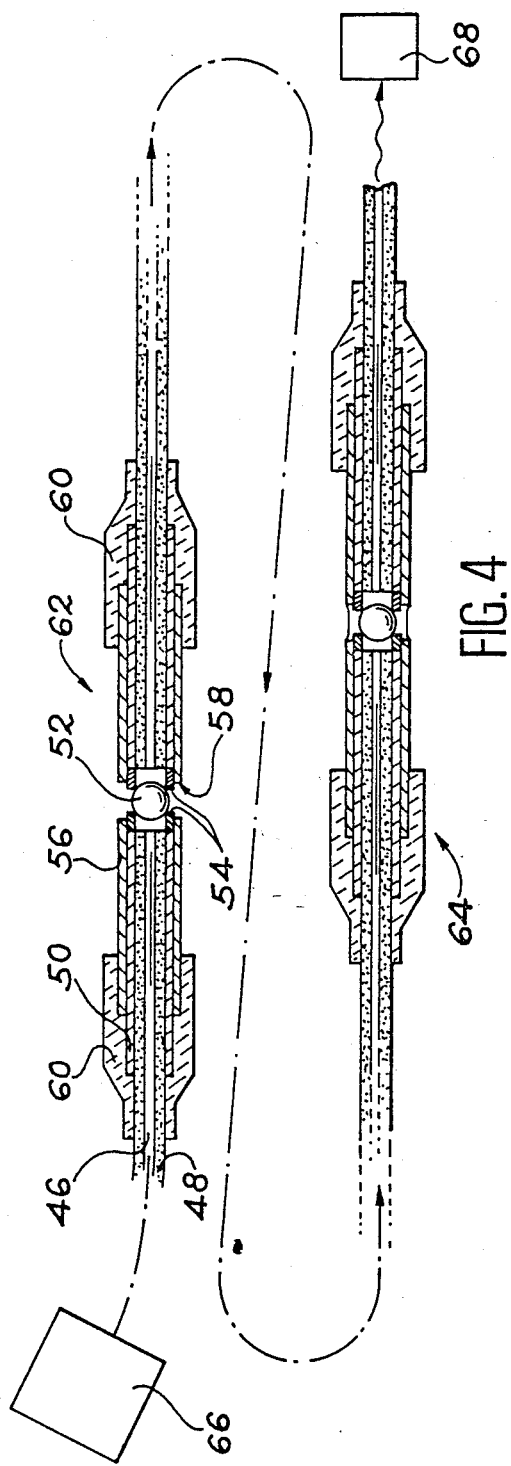
FIG. 3
FIG. 4

ACTIVE CHEMICAL TRANSDUCER WITH OPTICAL FIBRES AND REAGENT SUPPORTING MEANS

The present invention relates to an active chemical transducer with optical fibres. It is used in medicine, biochemistry and the agro-alimentary industry, for measuring the concentration of chemical species in fluid media, particularly for measuring the pH-values of liquid solutions, for measuring partial pressures of gases, such as oxygen or carbon dioxide gas in gaseous solutions, or for measurements of the optical index of fluid media (i.e. liquid or gaseous).

The transducer according to the invention, which is also called an optode, belongs to the category of so-called "active" transducers, as opposed to "passive" transducers, the latter only having one or more optical fibres and used as such as light guides and possibly associated with an optical system with a view to measuring a particular characteristic of a fluid medium.

Active transducers also have an appropriate reagent which, in contact with the fluid medium to be studied, interacts with light from the fibre (or one of the fibres). The study of the light resulting from this interaction makes it possible to arrive at the result of the measurement.

The reagent can be a substance, whose colour varies under the effect of the investigated characteristic of the considered medium and it is possible to observe this variation of colouring in absorption or fluorescence (reinforcement or extinction of the fluorescence, as a function of the reagent-medium chemical reaction used).

Optical fibre, active optical transducers are already known from U.S. Pat. No. 4,200,110, EP-A-0073558 and EP-A-0126600. The transducers described in these documents are intended for the study of liquid solutions and have at least two optical fibres placed in front of which is an appropriate reagent for the measurement to be performed on a given liquid solution, said reagent being immobilized or fixed to e.g. polystyrene particles. The assembly constituted by the reagent and these particles is contained in a volume delimited by a confining membrane, which is permeable to the ions contained in the liquid solution to be studied.

The optical transducers known from the aforementioned patents suffer from the disadvantage of requiring a membrane. The latter is prejudicial when it is necessary to sterilize the transducer, in view of the fact that it is generally made from an organic material, which does not satisfactorily resist temperatures equal to or higher than 125° C. Moreover, it limits the interaction speed between the reagent and the studied medium.

The object of the present invention is to obviate this disadvantage by proposing an optical fibre, active optical transducer using no membrane.

More specifically, the present invention relates to an active optical transducer with optical fibres used for measuring a given characteristic of a fluid medium, said transducer having at least one assembly with a reagent appropriate for said measurement and intended to interact with the fluid medium, means for supporting the reagent, an optical fibre called an emitting fibre for transmitting light in the direction of the support means and at least one other optical fibre called the receiving fibre and which serves to recover at least part of a backscattering, reflectance or fluorescence light from the support means when the latter receive the light from the emitting fibre, said transducer being characterized in that the support means comprise a single, completely porous and adsorbant member to which is fixed the reagent and which is placed facing the emitting fibre and each receiving fibre, said element being in direct contact through almost all of its outer surface with the fluid medium when the transducer is immersed in the latter, the said element consequently having no confinement membrane.

As the optical transducer according to the invention uses no membrane, it is possible to sterilize the transducer a considerable number of times and consequently reuse the same, which is important particularly in the agro-alimentary industry. Moreover, the absence of a membrane and the fact of having a quasi-total contact between the porous, adsorbant element and the fluid medium make it possible to have a high reaction speed between the reagent and the studied medium.

Moreover, in known transducers, it may be necessary to use membranes only permitting the passage of ions of a particular type. In the present invention, when the problem arises, it is sufficient to choose a very specific reagent for said ions.

It should also be noted that in the present invention use is made of a single porous, adsorbant element facing the fibres. This offers advantages compared with known transducers which use, as reagent support means, numerous microspheres e.g. formed from styrene-divinylbenzene copolymers. Such support means suffer from the disadvantage of being of a highly diffusing nature for light and therefore constitute a poor optical system for optical reflection or transmission measurements. The light energy recovered is then very small, which requires the use of intense exciting light sources and very sensitive photodetectors, such as photomultipliers or avalanche diodes. The use of a single porous, adsorbant element in the present invention makes it possible to obviate this disadvantage.

According to a particular embodiment of the transducer according to the invention, each assembly comprises several receiving optical fibres arranged parallel to the corresponding emitting optical fibre and on the same side as the latter with respect to the element of the assembly and which are distributed (preferably regularly) around the emitting optical fibre.

Such an arrangement of the receiving optical fibres around the emitting optical fibre makes it possible to collect a large quantity of diffuse light or fluorescence exciting light (as a function of the transducer type produced), which is not the case with the known transducers, which use a bundle of optical fibres, in which the emitting optical fibres and the receiving optical fibres are distributed in a random manner.

With such a special embodiment, it is then possible to produce a transducer according to the invention, incorporating a "parallel" arrangement of such assemblies, i.e. a transducer with several juxtaposed assemblies, which are rendered integral with respect to one another.

In an advantageous realization of the invention, corresponding to said "parallel" arrangement, each element is at least in part transparent and the transducer also comprises optically reflecting means placed on the other side of each element and which reflect part of the light from the support means in the direction of the receiving optical fibres via said support means. Therefore the receiving optical fibres can collect a large quantity of light.

According to another special embodiment of the transducer according to the invention, each element is at least partly transparent and each assembly comprises an emitting optical fibre and a receiving optical fibre arranged on either side of the element.

It is then possible to produce a first transducer according to the invention and which corresponds to said other special embodiment, whereby the first transducer has at least two assemblies placed in series and connected by a connecting optical fibre, which connects the receiving fibre of one assembly to the emitting fibre of the adjacent assembly. In a particular realization, the receiving fibre and the emitting fibre can be one and the same fibre forming the connecting fibre.

It is also possible to produce a second transducer according to the invention and which also corresponds to said other special embodiment, in which the transducer has at least two assemblies arranged in series in such a way that the transducer is continuous or in a single block, two adjacent assemblies having a common optical fibre serving as a receiving fibre for one and as an emitting fibre for the other.

In the present invention, on using several such assemblies, the reagents respectively associated therewith can differ from one another. This makes it possible to widen the measuring range, e.g. the pH measuring range for a transducer intended for carrying out pH measurements. Different reagents do not have the same spectral response as a function of the considered characteristic of a medium to be studied, e.g. as a function of the pH of a liquid. In the case of pH measurements and the use of two different reagents, said two reagents can be respectively fluorescein and bromophenol blue. It is thus possible to perform pH measurements at different wavelengths.

In a particular embodiment of the present invention, each element has an approximately spherical or ovoid shape.

In this case, each assembly can comprise a rigid sheath in which are fixed the element, the emitting fibre and each receiving fibre and which is provided with at least one opening facing each element.

As the element with an approximately spherical shape, it is advantageously possible to choose a porous silica ball (obviously of a size compatible with that of the optical fibres used). Such a ball permits repeated sterilizations of the transducer in question, whilst obviously choosing the other elements of the transducer and in particular the optical fibres, in such a way as to support or withstand such repeated sterilizations.

As has already been stated, the transducer according to the invention can be used for measuring the pH-value, each reagent then being a colorimetric reagent. In the case of such pH measurements, the reagent is advantageously thymol blue. Thus, the latter can be used both with a very acid solution (e.g. corresponding to pH-values between 0.5 and 3.5), said solution transforming the thymol blue from yellow to red, and with a very basic solution (e.g. corresponding to pH-values between 10 and 13), said solution transforming the thymol blue from yellow to blue.

Finally, in a particular embodiment of the invention, the transducer having three assemblies, said assemblies respectively have, as reagents, fluorescein, thymol blue and bromophenol blue (or phenol red), which are thus associated in the same transducer, which makes it possible to perform pH measurements over an extensive pH range.

The invention is described in greater detail hereinafter relative to non-limitative embodiments and the attached drawings, wherein show:

FIG. 1 a diagrammatic view of a particular embodiment of the transducer according to the invention.

FIG. 2 a diagrammatic view of a "parallel" assembly of several transducers according to the invention.

FIG. 3 a diagrammatic view of a "series" assembly of transducers according to the invention.

FIG. 4 a diagrammatic view of another "series" assembly of transducers according to the invention.

The transducers shown in FIGS. 1 to 4 are intended for performing pH measurements in liquid solutions, i.e. measurements of the concentrations of $H^+$ ions of said solutions, the reagents being coloured indicators immobilized on chemically inert porous supports of e.g. Amberlite (registered trademark). For example, optical absorption measurements are performed, the coloured indicators used having an optical absorption varying as a function of the pH of the investigated solution.

The transducers shown in FIGS. 1 to 4 can be used for performing concentration measurements on chemical species other than $H^+$ ions, provided that appropriate reagents for such measurements are chosen. In the same way, instead of performing optical absorption measurements it is possible to e.g. perform fluorescence or Raman spectrometry measurements. In a purely indicative and non-limitative manner, for performing measurements of the iron concentration in a liquid solution, it is possible to use a sulphur-impregnated, inert porous support, whilst for performing fluorescence measurements, it is merely necessary to impregnate an inert porous support with a fluorescent indicator.

FIG. 1 diagrammatically shows a transducer according to the invention. This transducer comprises a so-called emitting optical fibre 2 and several so-called receiving optical fibres 4, which are distributed around fibre 2. Fibres 2 and 4, which are preferably of silica, have parallel axes, are placed against one another and have in each case a planar end perpendicular to said axes, said planar ends being in the same plane. For miniaturization reasons, it is possible to remove from fibres 2 and 4 their generally plastic protective sheath over the entire length of the said fibres located within the transducer. For example, it is possible to use six receiving fibres disposed in accordance with a hexagonal configuration around the emitting fibre 2.

The transducer also comprises an e.g. stainless steel tube 6, in which are placed fibres 2 and 4, as well as an e.g. stainless steel cylindrical sheath 8, within which is placed the tube 6.

The transducer also comprises a single ball 10 facing said planar ends, e.g. made from a copolymer and having an appropriate reagent for the pH measurements, such as a coloured indicator, linked by covalence to the copolymer. The latter is advantageously of the polystyrene type, e.g. Amberlite (registered trademark) XAD 2 or XAD 4, of the styrene-divinylbenzene type or of the polyacrylamide type. It is also possible to use a porous silica ball and graphed on it the reagent by silanization (using methyloxypropyltrimethoxysilane). The use of a silica ball permits a sterilization of the transducer at high temperature. Obviously, it is necessary to provide the other transducer components in accordance with this. Thus, when the sheath is not removed from these fibres, e.g. polyimide sheath fibres are chosen.

Obviously, the diameter of ball 10 is chosen as a function of the diameter of the optical fibres. In a purely indicative and nonlimitative manner, use is made of one emitting fibre and six receiving fibres of silica, equipped with an e.g. polyimide protective sheath, the external diameter of said sheath being 320 micrometers. the core diameter of the fibres being 200 micrometers, the diameter of the optical sheath of said fibres being 280 micrometers and a ball diameter of 200 to 600 micrometers is chosen.

A first e.g. stainless steel tubular crosspiece or spacer 12, whose internal diameter and external diameter are respectively equal to the internal diameter and external diameter of tube 6, is fixed by one side to the latter, within sheath 8. Ball 10 is placed against the other side of the first spacer 12 and a second tubular spacer 14, identical to the first 12, is also placed in sheath 8, opposite to said first spacer 12 and against ball 10. Contacts between ball 10 and spacers 12 and 14 are not tight.

The transducer shown in FIG. 1 also comprises a solid cylindrical part 16, e.g. of stainless steel, whose diameter is very slightly smaller than the internal diameter of sheath 8. Part 16 penetrates sheath 8 from the side of spacer 14 and is fixed thereto, ball 10 being held and immobilized between the two spacers 12 and 14. When the ball is in place between the two spacers, a connection able to withstand repeated sterilizations is formed between the sheath 8 and part 16 by crimping the latter in sheath 8 or by bonding one to the other by means of an e.g. high temperature epoxy glue. In the same way, spacers 12 and 14 can be respectively fixed to tube 6 and part 16 by crimping or bonding by means of such a high temperature epoxy glue.

Level with ball 10, sheath 8 is also provided with windows 18, so that said ball 10 is in direct contact with the solution to be studied when the transducer is immersed in it.

Thus, when the end of the transducer corresponding to the ball is immersed in a fluid medium, the entire outer surface of the ball is in contact with said medium, except for a few points on said outer surface which are in contact with the spacers, hence the quasi-total contact of the outer surface of the ball with the fluid medium in question.

Face 22 of part 16 is advantageously made reflecting, e.g. by polishing, so as to reflect light reaching it from the ball in the direction of the latter.

The length of tube 6 is chosen in such a way that said tube passes beyond the other end of sheath 8. In said other end, the transducer comprises a holding element or sheath 24, which serves to confine said other end of sheath 8, the corresponding end of tube 6 passing beyond the same and a portion of fibres 2 and 4 passing out of said end of tube 6.

In order to realize the transducer shown in FIG. 1, it is possible to start by fitting the fibres 2 and 4 into the tube 6 provided with spacer 12, ball 10 (whilst holding everything vertically), sheath 8, sheath 24 and finally part 16 provided with the spacer 14. The transducer shown in FIG. 1 is used in the following way. The end of said transducer corresponding to ball 10 is immersed in the liquid solution, whose pH-value is to be determined. An appropriate light from light source 26 is injected into the emitting fibre 2 by the other end thereof. Said light reaches ball 10, whereof the reagent has reacted with the liquid solution and absorbs a certain light quantity.

Moreover, part of the light is reflected by ball 10 and again passes into the receiving fibres 4. Another part of the light traverses ball 10 (which is porous and impregnated with liquid solution), reaches the face 22 of part 16, is reflected thereon, again passes through ball 10 and focused by the latter, also passes into the receiving fibres 4. The light transmitted in this way by fibres 4 is analysed at the other end thereof by means of an appropriate photodetector 28.

The intensity of the light reaching photodetector 28 and which has the same wavelength as the light from source 26 is specifically dependent on the pH-value of the studied solution. It is then possible to determine the pH-value of the studied solution with the aid of said intensity and prior, appropriate calibrations of the transducer shown in FIG. 1. The latter has a simple design and can be manufactured in an inexpensive manner.

The fact that it is possible to use in said transducer optical fibres without their protective sheath makes it possible to miniaturize the transducer, so as to have a diameter of approximately 1 to 2 mm.

With respect to the use of the transducer shown in FIG. 1, it is pointed out that in order to overcome the background noise of the complete measuring chain, it is preferable to carry out measurements at two different wavelengths, in accordance with the principles of FR-A-2 317 638. For example, in the case of using thymol blue as the reagent, it is possible to carry out absorptivity measurements at 555 and 700 nm. A measurement at a supplementary wavelength (according to the principles of FR-A-2 474 166) makes it possible to obtain freedom from the ionic strength of the studied medium.

FIG. 2 diagrammatically shows a "parallel" assembly of several transducers according to the invention. The assembly e.g. comprises three transducers 30,32,34, each transducer having elements 2,4, 6,10,12 and 14 described with reference to FIG. 1. The relative arrangement of these various elements of transducers 30,32 and 34 is identical to that of the elements 2,4,6,10,12 and 14 of the transducer of FIG. 1.

Transducers 30,32 and 34 are identical and parallel to one another, each transducer being tangential to the two others. This last point is not apparent from FIG. 2 where, for reasons of clarity, the transducers 30,32 and 34 are shown in superimposed form.

The assembly shown in FIG. 2 also comprises a tubular stainless steel sheath 36, which confines the transducers 30,32 and 34. This sheath is provided with windows 38 revealing each ball 10, in such a way that the balls are in direct contact with the liquid to be studied, when the assembly of FIG. 2 is immersed therein.

This assembly also comprises a holding element 40, which confines an end of sheath 36 furthest from balls 10, the corresponding ends of the tubes 6, said ends of tubes 6 projecting beyond the considered end of sheath 36, and a portion of the groups of fibres 2,4, which pass out of said ends of tubes 6. It is pointed out that element 40 is the homolog of element 24 of FIG. 1. A filling material 42, e.g. high temperature epoxy glue, is placed within element 40 between the different groups of fibres 2,4, which pass out of said ends of tubes 6.

The assembly shown in FIG. 2 also comprises a cylindrical stainless steel part 44 for plugging the end of sheath 36 closest to balls 10 and for non-tightly engaging via the spacers 14 fixed thereto, the balls 10 against the spacers 12, which are themselves fixed to the corresponding ends of tubes 6. Part 44 can be glued to sheath 36, or can be crimped therein. Part 44 (which is the homolog of part 16 in FIG. 1) can be provided with an optically reflecting face facing balls 10.

In the case of a liquid solution to be analyzed, the assembly shown in FIG. 2 is immersed therein, appropriate light levels being respectively fed into the fibres 2 and are respectively recovered by the different groups of fibres 4 for analysis to carry out the desired pH measurements. To carry out the latter, the balls 10 can e.g. be provided with different reagents (e.g. fluorescein, thymol blue and bromophenol blue).

Obviously, the assembly shown in FIG. 2 can have more than three transducers 30,32,34 and for example seven transducers like 30,32, 34, which are parallel to one another and arranged in accordance with a hexagonal configuration. (Six transducers are associated with the apices of a hexagon and a seventh transducer with the centre of said hexagon).

FIG. 3 diagrammatically shows a "series" assembly of transducers according to the invention. This assembly 45 comprises a preferably silica optical fibre 46 having a plastic protective sheath 48, as well as a stainless steel tube 50 confining the fibre. The tube and fibre are interrupted at several points, e.g. at two points. Each free fibre and tube surface corresponding to these interruptions is in the same plane perpendicular to the common axis of the fibre and tube. Balls 52 like ball 10 in FIG. 1 are placed in each of the interruptions. Each ball is held (non-tightly) between two stainless steel spacers 54, which have the same internal diameter and the same external diameter as tube 50 and which are respectively fixed to the free surface of said tube corresponding to the considered interruption.

The assembly shown in FIG. 3 also comprises a stainless steel tubular sheath 56, which confines tube 50 and which is provided with windows 58 level with balls 52 and serving to permit a direct contact between a liquid to be studied and the balls when the assembly shown in FIG. 3 is immersed in said liquid.

This assembly also comprises two holding elements 60, which confine the ends of sheath 56, the corresponding ends of tube 50 passing beyond said ends of sheath 56, and the portions of fibre 44 respectively passing out of the ends of tube 50.

Balls 52 can be provided with different reagents and when the assembly is immersed in the liquid solution in which it is wished to carry out the pH measurements, by injecting an appropriate light at the end of fibre 46, said light traversing the fibre whilst successively traversing the different balls and interacts with the reagent placed on each of them, so that at the other end of the fibre 46, it is possible to carry out a wavelength analysis of the recovered light (e.g. using a monochromator and photodetector, which are not shown), information being obtained on the pH of the solution in the vicinity of each of the balls.

The assembly shown in FIG. 3 can be obtained by firstly producing the said interruptions on the fibre, then putting into place one of the two holding elements 60 and then the corresponding portion of tube 50, equipped with the spacer associated therewith, followed by the corresponding ball 52 (two portions 50 being vertically held), sheath 56, the tube portion 50 resulting from two interruptions, equipped with the fibre portion corresponding thereto and two spacers fixed at its ends, the other ball 52 and finally, by putting into place the other element 60 on the remaining portion of the fibre and on the corresponding portion of the tube equipped with its spacer and by forcing into said corresponding end of sheath 56 said tube portion until the other element 60 confines sheath 56.

It would obviously be possible to produce an assembly with more than two fibre interruptions and therefore more than one central fibre section.

FIG. 4 diagrammatically shows another "series" assembly of transducers according to the invention. This other assembly comprises, like the assembly shown in FIG. 3, an optical fibre 46 having a protective sheath 48, said fibre being interrupted e.g. at two points. With each interruption is associated a transducer according to the invention, so that the two transducers 62 and 64 are obtained. These two transducers are identical, except for the reagents associated therewith, which can be different.

Each transducer 62 or 64 is also structurally identical to the assembly shown in FIG. 3, in which one of the two balls and the "central section" of said assembly have been removed. In other words, each transducer 62 or 64 comprises on passing from one end to the other thereof, an element 60, a tube portion 50 containing a fibre part serving as an emitting fibre, a spacer 54, a ball 52, another spacer 54, another tube portion 50 and another element 60, as well as a sheath 56 held in the two elements 60 and surrounding the two tube portions 50, the sheath being provided with windows 58 at ball 52 to permit a direct contact between the ball and the liquid solution to be studied when the assembly is immersed in it. The other tube portion 50 contains a fibre portion serving as the receiving fibre, the receiving fibre of transducer 62 being extended beyond the same and penetrating transducer 64 in order to constitute the emitting fibre thereof.

As for the assembly shown in FIG. 3, the pH measurement is performed by immersing the assembly of FIG. 4 in the liquid solution to be studied, by injecting at one end of fibre 46 (on the side of transducer 62) an appropriate light from a light source 66 and by studying the light recovered at the other end of fibre 46 (on the side of transducer 64) using appropriate photodetection means 68, e.g. incorporating a not shown monochromator.

The optical fibre length between the two transducers 62,64 can be significant, e.g. about 50 meters or more. Moreover, it is obviously possible to produce an assembly having more than two transducers of type 62 and 64 and being in series.

In the assemblies shown in FIGS. 2, 3 and 4, it is possible to use different reagents in pairs having specific differentiatable spectra, the measuring means used respectively with these different assemblies being chosen as to have adequate scale dynamics. In a purely indicative and non-limitative manner for a "series" assembly of two transducers, it is possible to use a dye able to change from yellow to red and another dye able to change from yellow to blue in an acid medium.

The assemblies of "series" transducers are advantageous, because they make it possible to increase the measurable pH range. Thus, each of the usable dyes is generally sensitive to 2.5 pH units. A multiplicity of transducers connected in series consequently makes it possible to obtain a large pH dynamics for the assembly obtained.

What is claimed is:

1. Active chemical transducer with optical fibres, for measuring a given characteristic of a fluid medium, said transducer having at least one assembly with a reagent appropriate for said measurement and intended to interact with the fluid medium, support means for supporting the reagent, an optical fibre, calling the emitting fibre and used for transmitting light in the direction of the support means and at least one other optical fibre, called the receiving fibre, which recovers at least part of the light from the support means, when the latter receive the light from the emitting fibre, wherein the support means have a single, membraneless, completely porous and adsorbing element, to which is fixed the reagent and which is positioned facing but spaced from the emitting fibre and each receiving fibre, substantially all of the outer surface of said element being unconfined and in direct contact with the fluid medium when the transducer is immersed in the latter.

2. Transducer according to claim 1, wherein each assembly comprises several receiving optical fibres, which are arranged parallel to the corresponding emitting optical fibre and on the same side thereof with respect to the element of the assembly and which are distributed around the emitting optical fibre.

3. Transducer according to claim 2, wherein it comprises several assemblies, which are juxtaposed and rendered integral with one another.

4. Transducer according to claim 2, wherein each element is at least partly transparent and wherein the transducer also comprises optical reflecting means placed on the other side of each element and which reflect part of the light from the support means in the direction of the receiving optical fibres via said support means.

5. Transducer according to claim 1, wherein each element is at least partly transparent and wherein each assembly comprises an emitting optical fibre and a receiving optical fibre arranged on either side of said element.

6. Transducer according to claim 5, wherein it comprises at least two assemblies arranged in series and connected by an optical connecting fibre, which connects the receiving fibre of one assembly to the emitting fibre of the adjacent assembly.

7. Transducer according to claim 5, wherein it comprises at least two assemblies arranged in series in such a way that the transducer is continuous, two adjacent assemblies having a common optical fibre serving as the receiving fibre for one and the emitting fibre for the other.

8. Transducer according to claim 3, wherein the reagents respectively associated with the assemblies differ from one another.

9. Transducer according to claim 1, wherein each element has an approximately spherical or ovoid shape.

10. Transducer according to claim 9, wherein each assembly comprises a rigid sheath, in which are fixed the element, the emitting fibre and each receiving fibre and which is provided with at least one opening facing each element.

11. Transducer according to claim 9, wherein each element is a porous synthetic resin ball.

12. Transducer according to claim 9, wherein each element is a porous silica ball.

13. Transducer according to claim 1, wherein it is intended for measuring a pH-value and wherein each reagent is a colorimetric reagent.

14. Transducer according to claim 13, wherein said reagent is thymol blue.

15. Transducer according to claim 8, wherein it comprises three assemblies respectively having as reagents fluorescein, thymol blue and bromophenol blue or phenol red.

16. Transducer according to claim 6, wherein the reagents respectively associated with the assemblies differ from one another.

17. Transducer according to claim 7, wherein the reagents respectively associated with the assemblies differ from one another.

18. Transducer according to claim 1 wherein the support means for supporting the reagent comprise said element and means for engaging and supporting said element so as to maintain said element in spaced apart relationship from both the emitting fibre and each receiving fibre, said means for engaging and supporting said element functioning in such a way as to expose substantially all of the outer surface of said element to the fluid medium.

19. A transducer according to claim 18 wherein said means for engaging and supporting said element makes line or point contact with said outer surface of said element.

20. A transducer according to claim 19 wherein said means for engaging and supporting said element comprises tubular means having an end engaged with said outer surface of said element and making line or point contact therewith.

21. A transducer according to claim 20 wherein said element is spherical or ovoid in shape and said end of said tubular means is annular in shape.

* * * * *